United States Patent
Voegeli et al.

(10) Patent No.: US 6,735,551 B2
(45) Date of Patent: May 11, 2004

(54) SYSTEM FOR MAINTENANCE AND MANAGEMENT OF HEALTH

(76) Inventors: Fridolin Voegeli, Aegertlistrasse 19, CH-8800 Thalwil (CH); Fredrick J. Mindermann, 9401 Glen Ridge Dr., Brentwood, TN (US) 37027

(*) Notice: Subject to any disclaimer, the term of this patent is extended or adjusted under 35 U.S.C. 154(b) by 0 days.

(21) Appl. No.: 10/312,317
(22) PCT Filed: Jun. 22, 2001
(86) PCT No.: PCT/IB01/01110
§ 371 (c)(1), (2), (4) Date: Dec. 20, 2002
(87) PCT Pub. No.: WO01/97686
PCT Pub. Date: Dec. 27, 2001

(65) Prior Publication Data
US 2003/0101078 A1 May 29, 2003

(30) Foreign Application Priority Data
Jun. 22, 2000 (WO) ................ PCT/IB00/00838

(51) Int. Cl.⁷ .................... G06F 19/00; G06F 17/00
(52) U.S. Cl. .................... 702/183; 705/2; 128/920
(58) Field of Search ................ 702/183, 188; 705/2, 3; 600/301, 300; 128/920, 923, 924, 925

(56) References Cited

U.S. PATENT DOCUMENTS

| | | | | | |
|---|---|---|---|---|---|
| 5,544,661 | A | * | 8/1996 | Davis et al. | 600/513 |
| 6,277,072 | B1 | * | 8/2001 | Bardy | 600/300 |
| 6,602,469 | B1 | * | 8/2003 | Maus et al. | 422/68.1 |
| 2001/0012913 | A1 | * | 8/2001 | Iliff | 600/300 |
| 2001/0047125 | A1 | * | 11/2001 | Quy | 600/300 |
| 2002/0013518 | A1 | * | 1/2002 | West et al. | 600/300 |
| 2002/0019584 | A1 | * | 2/2002 | Schulze et al. | 600/300 |
| 2002/0072932 | A1 | * | 6/2002 | Swamy | 705/2 |
| 2002/0147390 | A1 | * | 10/2002 | Markis et al. | 600/301 |
| 2002/0169584 | A1 | * | 11/2002 | Fu et al. | 702/188 |
| 2002/0188182 | A1 | * | 12/2002 | Haines et al. | 600/300 |
| 2002/0198473 | A1 | * | 12/2002 | Kumar et al. | 600/595 |
| 2003/0036683 | A1 | * | 2/2003 | Kehr et al. | 600/300 |
| 2003/0069751 | A1 | * | 4/2003 | Lichtenstein et al. | 705/2 |
| 2003/0153819 | A1 | * | 8/2003 | Iliff | 600/300 |

FOREIGN PATENT DOCUMENTS

| US | pct/us99/26473 | * | 5/2000 | G06F/19/00 |
|---|---|---|---|---|
| WO | WO 00/28459 | | 5/2000 | |

* cited by examiner

Primary Examiner—Patrick Assouad
(74) Attorney, Agent, or Firm—Janet Sleath; Ann W. Speckman

(57) ABSTRACT

The present invention relates to a Mobile Tele-Medical Maintenance system (MTMM system) that applies different IT methods to perform different functions for the telemedical maintenance of large numbers of individuals. The MTMM system includes a system kernel residing on web servers, linked to a large number of peripheral units on the individuals. The kernel contains a collection of all the "Private Medical Web Sites" and "Personal Health Plans" of the individuals. The MTMM system periphery includes walk-in care offices and intelligent physiological sensors that can communicate directly with the kernel's programs via the Internet or similar communication networks, preferably using the user's phone and its traditional interfaces, message display plus message voice, and push-button plus voice input. The system kernel controls the actuators directly in the periphery and uses message display and message voice output of the telephone to interact with the individual.

9 Claims, 4 Drawing Sheets

SYSTEM FOR MAINTENANCE AND MANAGEMENT OF HEALTH

FIELD OF THE INVENTION

The present invention relates generally to systems for maintenance and management of health for individual patients including Communication Systems for remote monitoring and controlling of large collections of individuals, persons or devices, and is also related to Artificial Intelligence for managing and maintaining the patient's good status and trouble-free health.

BACKGROUND OF THE INVENTION

In most western societies, namely the United States and Europe, more than 30% of the population have serious chronic health problems that challenge them in many aspects of their daily lives, especially when they are working, traveling, or playing sports. The annual medical cost in the U.S. has soared to more than $10,000 per person with health problems. To lower and control these costs, home and preventive healthcare programs have been launched and promoted by insurers and politicians that are delivered by mostly small local caregivers at different locations in the country. The success of these programs was expected to be significant, especially when modern tools and methods of communication were designed, as described in earlier patents, for different, interactive and interesting hardware systems and electronic data processing, or, EDP methods.

But all these efforts do not escape the fact that life expectancy has climbed faster than any corrective measures. Sooner or later we will nearly all be a part of the group of persons who have to be constantly monitored. In these modern societies we mostly live on our own with no other person in the home. Also, many retired people's homes will only accept us if we can still move around freely and do not have to stay and be served in bed all the time, because the next weakness or dizziness cannot be predicted or immediately assessed and reacted upon.

Many tele-medical systems have been designed and described in detail, but they have not really been widely used and have not contributed to successful optimization of costs and services. The main reason for this is the limited use of existing technology in hardware and software by medical caregivers and therefore only a limited range of services are conceived and delivered.

SUMMARY OF THE INVENTION

An object of the invention is to provide a system for the maintenance and management of health which permits easy and complete access to all important data of the patient to be treated. The system comprises condition monitoring devices that measures physiological data of a patient; a supervision device that assesses the measured physiological data and transmits alarm signals and event information to caregivers; an evaluating device that compares problems and patterns of the measured physiological data and provides the caregivers with recommended corrective action; and a communication system that transmits alarms and recommendations to a supervisor.

The main advantage of the system according to the present invention is that all important data can be retrieved immediately at any location so that caregivers such as doctors and emergency services personnel can immediately decide which treatment or therapy to give.

Systems used for the management of large industrial plants such as those used to control and maintain large oil refineries, or to monitor remote pump stations along pipelines have been known for 20 year. Such systems utilize the latest sensor technology with high-speed communications and extensive Artificial Intelligence in central supervision stations. Repair and preventive maintenance costs have been reduced to the lowest optimized levels, while availability of very complex plants has increased and can be guaranteed today to 100% over 30 years.

The functions to be implemented in an efficient and optimized health maintenance system of large groups for individuals, spread over rural areas, are very similar to management systems that secure the safe and efficient operation of all the installations in a large metropolitan subway system. The medical maintenance system according to the present invention combines the advantages of standard medical sensors and well-trained medical personnel in hospitals, doctor's offices, wide-spread walk-in clinics, and emergency services with the leading technical maintenance intelligence with the most efficient and most widely used traditional communication tool, the telephone.

These and other advantages of the invention are disclosed in the following description in which an exemplified embodiment of the invention is described with respect to the accompanying drawings.

DETAILED DESCRIPTION OF THE INVENTION

In the following description, 'patients', 'individuals' and 'units' are defined as the individuals and the large number of distributed entities to be monitored, managed and maintained. They all have a 'condition', which is defined by the physiological data and is measured through different parameters. The term 'walk-ins' refers to the devices, doctor's offices and labs, that measure and collect the 'condition' data from the 'patients' by 'sensors'and feed the measured data into the health maintenance and management system.

The system's programs are referred to as 'managers'. The terms 'supervisors' and 'caregivers' refer to the persons in charge of the 'condition' monitoring such as doctors and emergency services personnel. The 'supervisors' and 'caregivers' react on 'events', which are defined as alarms, problems and the like. 'Resources' are defined as the man hours, money, people, devices, energy, and consumables or disposables used and spent for treating, troubleshooting, assisting, teaching, and maintaining the 'units'.

'Logs' are defined as all the electronically organized and recorded inputs of the measurements, actions, notes, and results. 'Reports' are defined as all the information gathered over time and compiled for different purposes to satisfy general and specific information needs, such as administrative functions, strategic fact-finding, and decision-making.

MTMM System Overview

Figure 1:
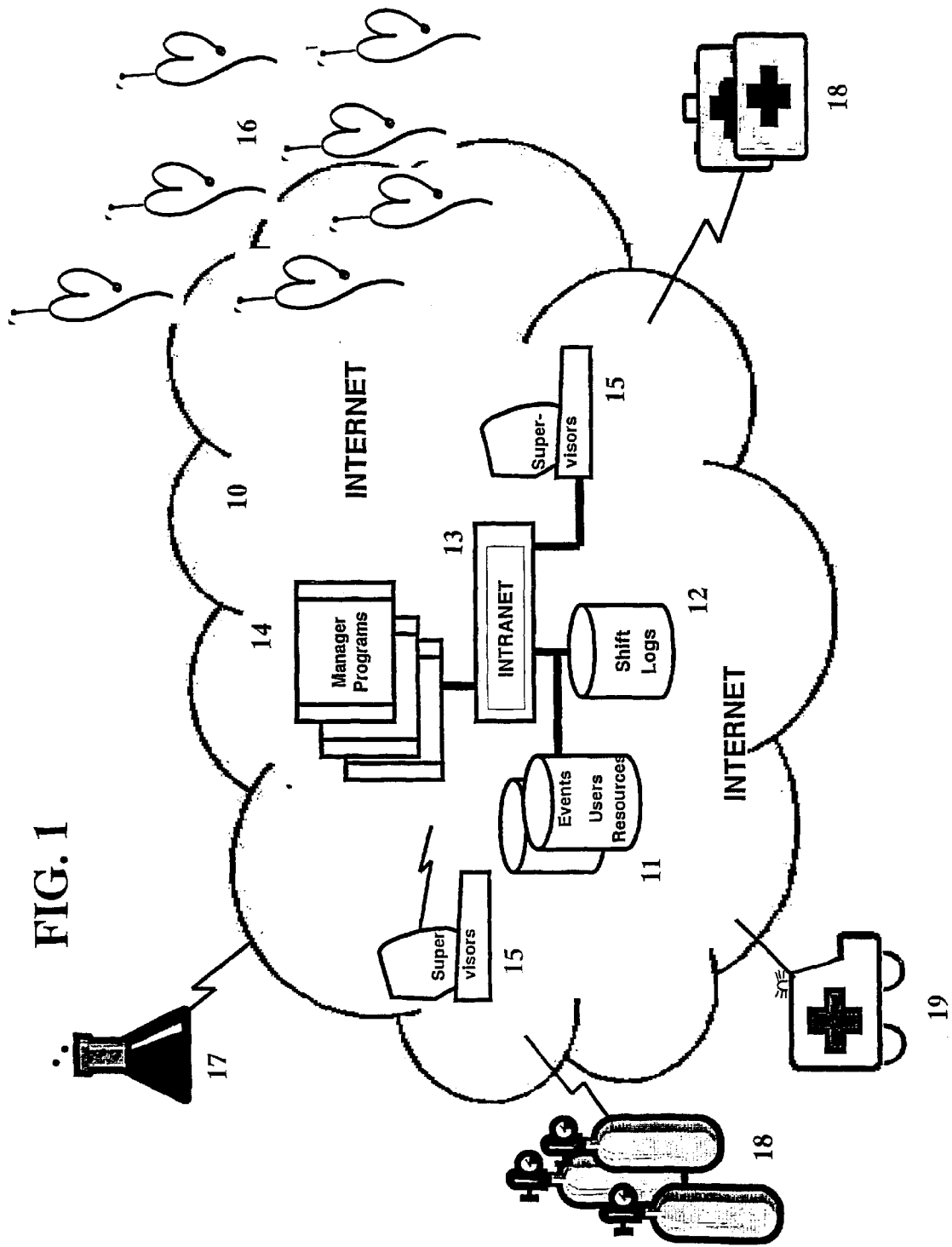
FIG. 1 shows an overview of the elements of a health maintenance and management system of the present invention.

In FIG. 1, a platform of the Mobile Tele-Medical Maintenance System (MTMM) is depicted. The MTMM is a computer system that combines proven technology process control modules, hardware and software with a known medical knowledge base, linked via the Internet 10. The telephone is used as a communication net and backbone to the distributed peripheral entities. The system kernel consists of several large databases 11 containing all the relevant data of all the patients and resources. A 'Personal Medical Web Site' containing the data in the form of an EMR ('Electronic Medical Record') is stored in a condition log in one of the databases 11. Access to the EMR can be obtained via an Internet link. The system kernel, which normally resides on web servers is also linked to a large number of peripheral units on the individual patients.

A 'Personal Health Plan' shows all the doctor's prescriptions and recommendations to the patient, including the patient's medication, diet, physical activities, lifestyle, the Patient's telephone calls to the doctor's office, etc. A selected condition monitoring contains threshold values or limits and indications for corrective actions that are available to caregivers should any values or limits be exceeded.

A further database 12 collects all the condition measurements made and event messages received, together with all the corrective actions or reactions taken and initiated by the manager programs, the supervisors and caregivers, and links them to the cases, users and resources in a Shift Log. The Personal Health Plan is also linked to the Shift Log. The databases 11 and 12 are connected by and communicate with each other over an internal network or intranet 13, directed by manager modules 14, supervisors, and caregivers 15.

The kernel is surrounded by peripherals linked to the databases and the Manager Modules via the Internet. The peripherals include all the patients, shown as 'mobile hearts' 16, the walk-ins 17, the caregivers 18 and emergency services 19. These peripherals have many ways to enter their condition data into the databases using, for example, smart Sensors, lab instruments, PC's, alarm buttons, or helpphones. They may also enter the condition data into the database by manually typing or by voice inputting the plain text on a terminal. Also, scanners can be used to enter handwritten information into the databases 11, 12. The information can be transposed into machine-readable information by a known transposing program and transferred to databases 11, 12.

Log Manager Module

Figure 2:
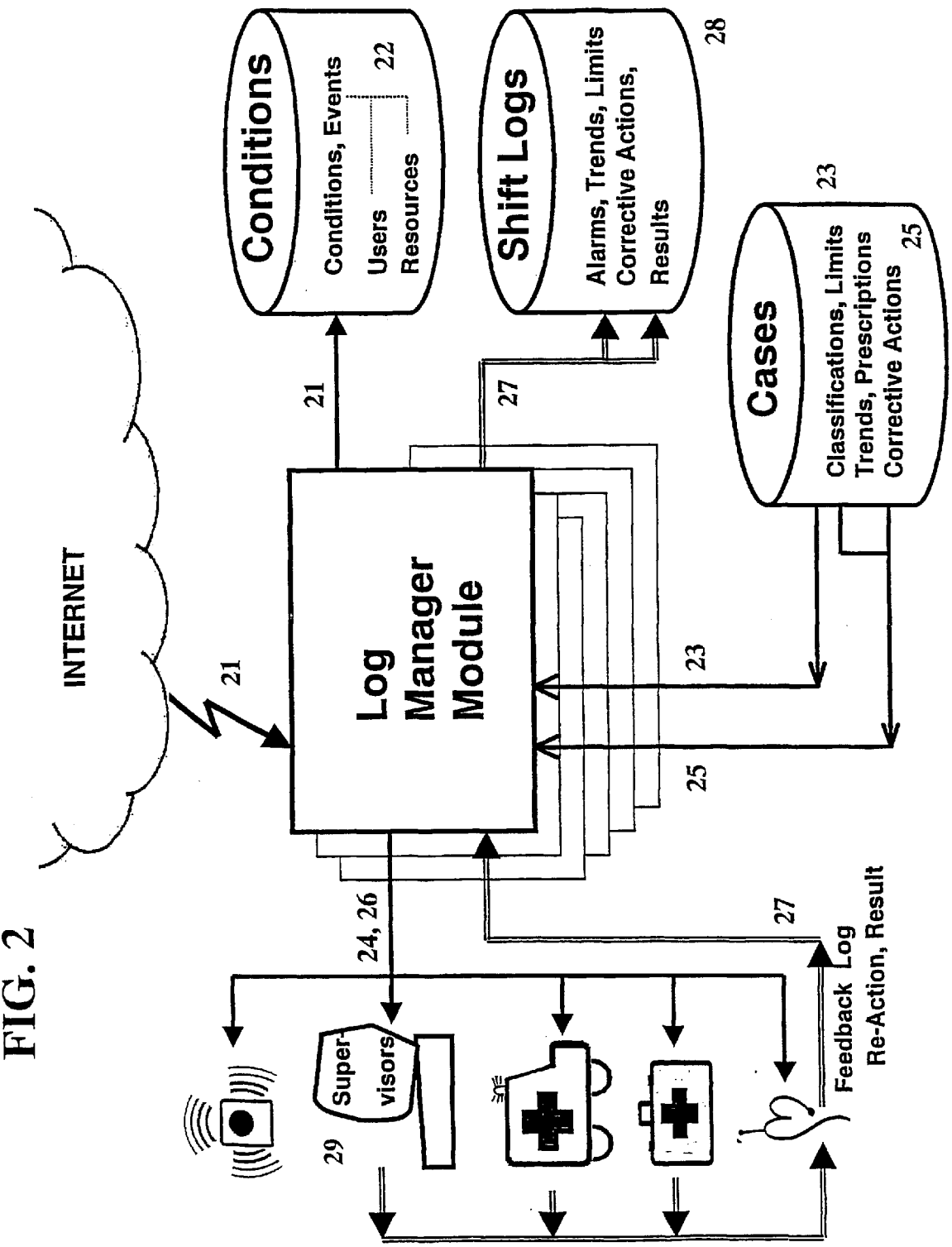
FIG. 2 shows a basic program module of the inventive health maintenance and management system for monitoring and supervising.

In FIG. 2, a Log Manager Module is shown. The Log Manager Module the basic program module of the MTMM system, and performs condition monitoring and supervision. All conditions, such as measurements, alarms events 21, and other inputs, are entered and logged into the databases. All the necessary links 22 to the Personal Health Plans are updated, which enables fast retrieval and augmentation of knowledge stored in a knowledge database.

The Log Manager Module is a condition monitoring device that may assess the data entered. If the patient's preset limits or trends 23 are exceeded, the module automatically generates alarms 24 to supervisors, caregivers, patients, emergency services, and other medical personnel on duty. Based on the doctors' prescriptions 25 and case classifications 23, the Log Manager Module initiates telephone calls by doctors, visits by caregivers, medication changes by pharmacies, device exchanges, and maintenance by technicians, etc.

The Log Manager Module also sends orders 26 for these corrective actions to the human shift supervisor, who may then decide on priorities and may coordinate the actions. The Log Manager Module keeps track of all the related events, such as the module's own actions and initiations, the supervisor's decisions, the actions and the results feedback 27, in a fully integrated shift log 28. It is a main characteristic of the MTMM system that all the tasks either can be or must be executed in parallel by the software manager modules and the human supervisors.

The Log Manager Module is an excellent tool for any shift supervision 29 and for medical supervision. No handwritten notes are necessary because all important events are always present in the module and can be called upon directly on-screen. The planning of shifts in care giving, emergency telephone services, for ambulances, and for hospitals, etc. becomes easier to manage.

Diagnostic Manager Module

Figure 3:
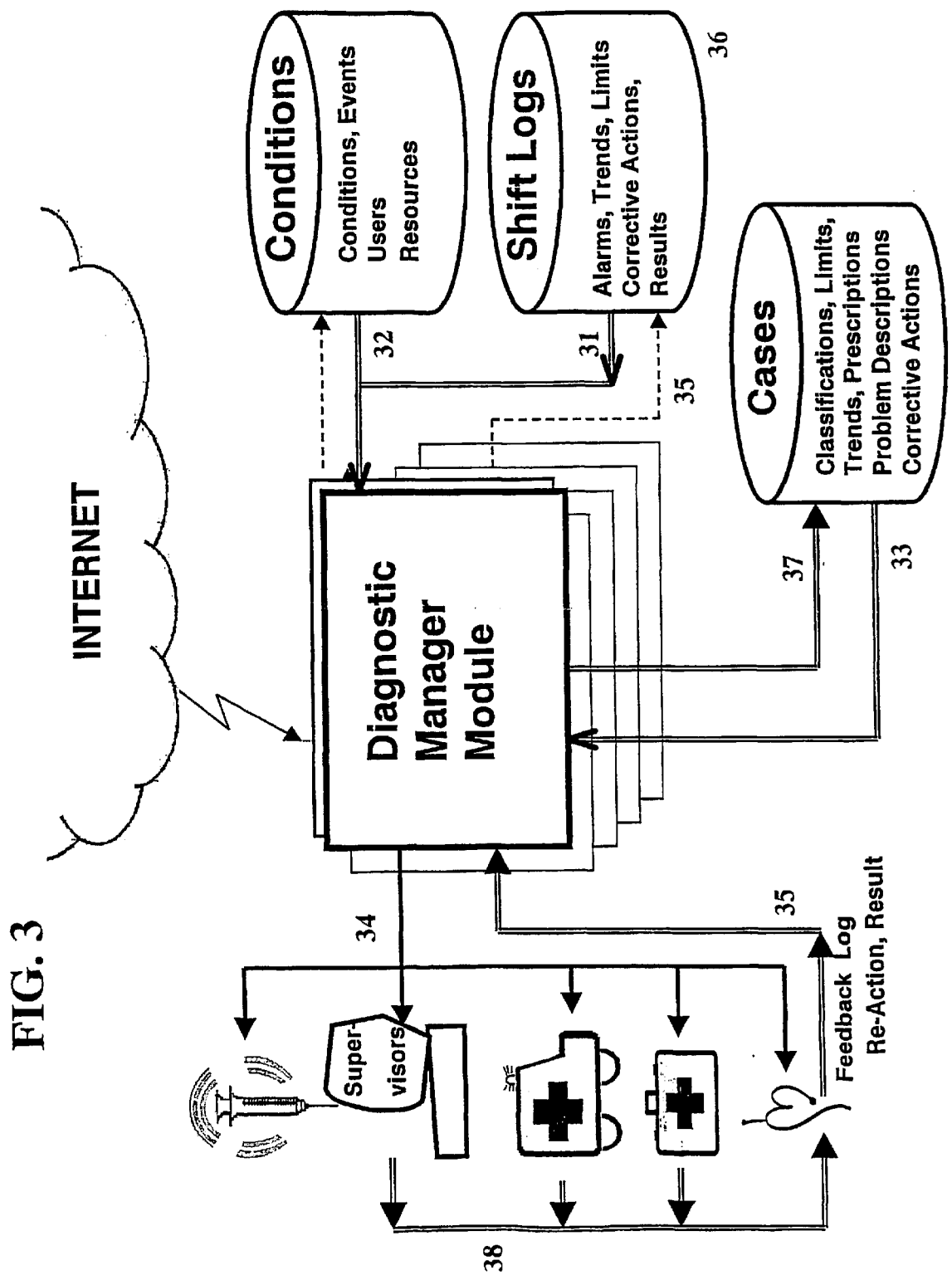
FIG. 3 shows another module of the inventive health maintenance and management system for assessment and decision making.

FIG. 3 shows the Diagnostic Manager Module as an evaluating device, which is a 'knowledge driven brain' of the MTMM system. The module assesses the conditions and events, takes decisions, and makes recommendations to the caregivers and the patients for troubleshooting, and treatment, and keeps records of the results 35 of each action.

In response to the alarms 31, condition measurements 32, and descriptions 33 of problem situations, the Diagnostic Manager Module enables supervisors, caregivers, emergency technicians, and patients to assess the situation 34 and to identify the appropriate corrective action quickly and accurately. This module, by applying standard software technologies, combines the actual 'best-practice' diagnosis guidelines with a unique knowledge database from electronic Shift Logs 36, while learning and acquiring new knowledge 37 continuously.

With this knowledge always recallable from the Diagnostic Manager Module, all the supervisors, caregivers, emergency and shift staff are learning continuously while they are on their jobs 38, reducing significantly the cost of training while improving the quality of their services. Internet-based teaching can be included, linked, and added to the recommended procedures.

Health Plan Manager Module

A Health Plan Manager Module functions as the first program in the 'Maintenance Control Cycle'. The module enables the Caregivers to tailor-make their 'teaching and treatment' services to the patients' individual needs, while optimizing the deployment of their resources and reducing costs. This module is also the follow-up program that enables the caregiver and the patient to adjust their efforts and to optimize the deviation of the condition from the accepted 'best practice' standards for the patient's sex, age, population group, job, education, activity, etc.

All teachings, treatments, medications, activities, and condition monitoring parameters associated with the devices and actions are managed and displayed to the caregivers and patients in a Personal Health Plan (or Disease Management) classification system. All the different sources of services (doctors, walk-ins, caregivers visits) and the care and assistance given, both planned and unplanned, are selected and implemented in this 'Personal Health Plan'. For this task, the Health Plan Manager Module draws on the caregivers' experience, the 'best-practice' guidelines, and also on all company internal rules, and ISO certified standards.

The 'Personal Health Plan' keeps the overall picture of all the service efforts performed and the resulting condition, which is summarized into an integral history of the patient's health. Transitions in a patient's 'medical life', such as visiting the hospital, entering into a nursing home, moving to a different area, changing family doctor, changing job, and acquiring new health insurance, etc., can be managed without transferring the patient's data in a old-fashioned, cumbersome way. In the MTMM system, the 'Mobile Patient' can really leave home 'without it' and be able to access his 'Private Patient Web site' and his 'Personal Health Plan' from any location in this world, while still being able to be monitored, supervised and assisted as if he were in his hometown.

Service Manager Module

The Service Manager Module is designed for the caregiver's logistics organization. The module allows the caregivers to monitor and optimize their highly complex, distributed and costly operations. It manages the collection of all service contracts and doctors' prescriptions. It also controls all the preventive care and unscheduled troubleshooting events, by including the events in an "integral" care cycle. In addition, the module allows regular preventive care work to be scheduled, planned, ordered, and monitored down to the smallest consumable needed.

All services, devices, and resources are recorded and managed in a parts classification system. This system includes all necessary information about suppliers, contracts, equipment and warranties. Like the way the Health Plan Manager Module manages all the patients, planned or unplanned care and peripheral entities, the Service Manager Module also manages and maintains the devices and resources ready for use. For this purpose, the Service Manager Module also contains all the information relating to ISO standards and company internal rules and specifications.

While the caregivers perform their work, all data about the type of service, the methods used to solve the problems, the type and the cost of the medication and material used are entered into the module and a special care service report is generated. Findings, conclusions, and actions taken are then transferred to the Diagnostic Manager's knowledge database.

Report Manager Module

The Report Manager Module is the evaluation and analysis program for the management of this fully integrated health maintenance process. It enables continuous and periodical monitoring and classification of the activities in the electronic Shift Log, in the service orders, and in the other events. This module gives a clear picture of the patients and the population group's proneness to problems as well as the cost control, hours spent, and medication and consumables used.

The Report Manager Module also enables monitoring of the compliance of the therapies implemented and the outcome of the therapies administered. It therefore delivers a basis for all measures to improve efficiency and quality of the caregiving process ('teaching and treating') throughout the whole service industry and its market.

All the databases are of the relational type, based on standard software. It is therefore easy to add report generators to create additional, custom made reports, as well as to implement interfaces to sophisticated Management Information Systems.

Peripherals Integration

Figure 4:
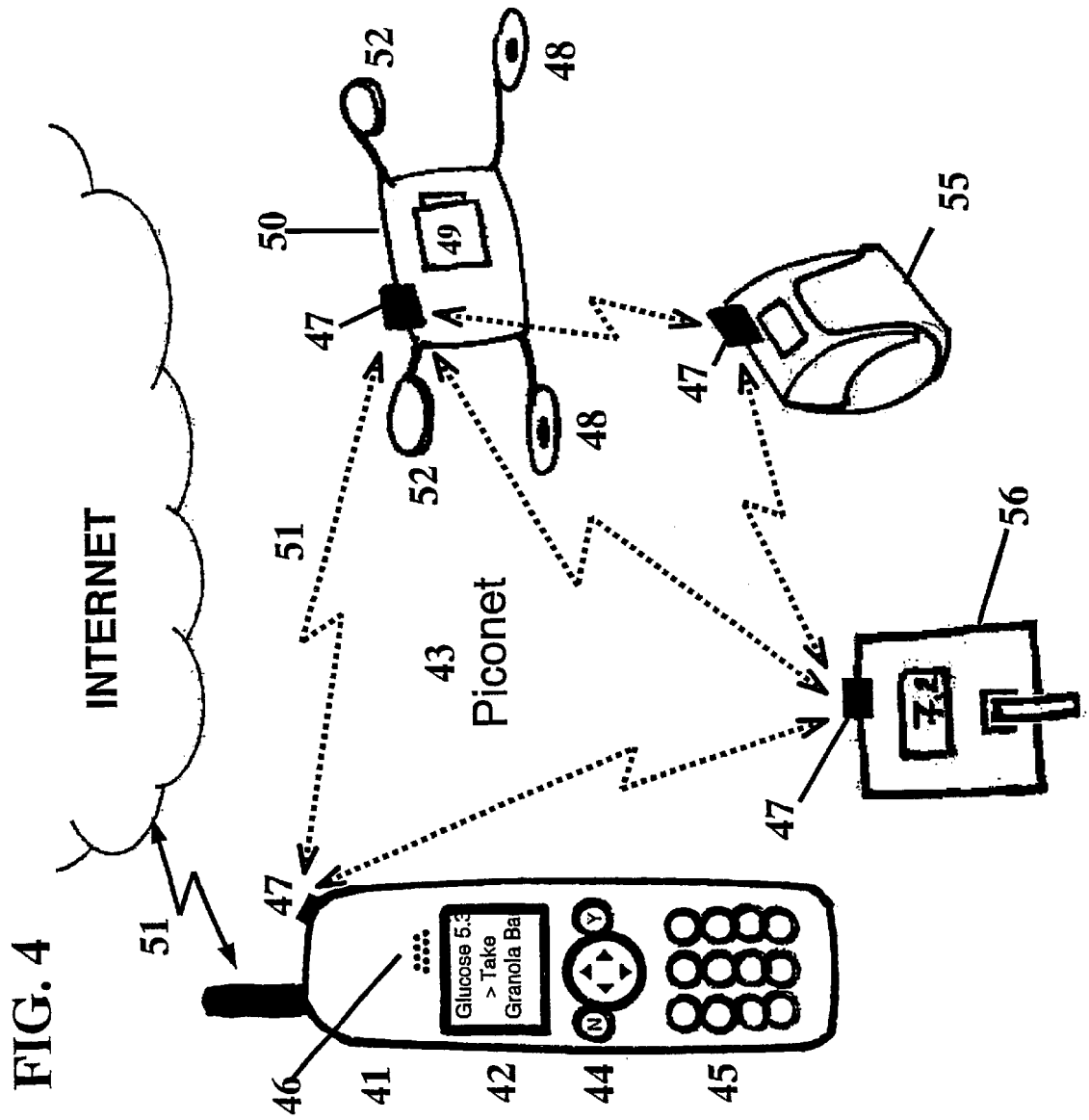
FIG. 4 shows several medical sensors connected to a mobile telephone for communication with the inventive health maintenance and management system.

In FIG. 4, the integration of peripherals is depicted. The MTMM system uses the open architecture of the Internet, the telephone and the so called 'RF-Piconet', to finally enable a full integration of all types of peripherals via the easy to use and omnipresent wired or wireless telephone link.

The telephones, mainly the new mobile phones, (also built into other devices, such as watches and palm PC's), shall become the preferred devices to use in personal medical condition monitoring systems. Installing and assigning new peripherals is easy: new users receive telephones with a world-wide private number (=device address). These telephones can be used anywhere with any telecom company's infrastructure.

These new mobile phones have become real Internet terminals, with which huge amounts of information can be downloaded and displayed, if necessary. The mobile phones are used in the MTMM system as hubs for the very small network of different intelligent sensors, called "Piconet" 43, located on the patients' body and in devices nearby at home. The mobile phone can poll, display, pre-assess, and transmit the condition data from the sensors to the databases in the kernel. Users have long been comfortable with the telephone's user-friendly guidance system of: "if you need assistance, press 0", and will also get used to high-tech voice input and voice recognition technology.

In most urban areas, the mobile phone system enables accurate tracking of the patient's position with an accuracy of approximately 50 meters, which is not only an ideal tool for any emergency medical service personnel, but also for caring friends and family members.

The sensors have become 'intelligent' and can communicate over the same Internet with the central Log Manager Module. In the MTMM system, the sensors can download requests and limits for bio-signal acquisition and transmission, and perform the condition monitoring. The sensors can perform basic pre-assessments of the bio-signals and can set off local alarms to the patient, if threshold limits of the bio-signals are exceeded. The sensors integrate RF-Piconet transceivers (like Bluetooth) which enable them to start communication with any other device, whenever they are switched on.

The MTMM system thus performs the functions of "CSACT": Condition monitoring, Supervision, Assessment, Communication, Treatment and Teaching. The system applies different methods of signal analysis in the intelligent sensors and in the kernel to assess the actual status of individuals. The system communicates the assessment to diagnosing programs and supervisory personnel, and commands the actuators, the assistance personnel, and the individual patient to treat himself or herself while coping with the actual situation. Using standard and Artificial Intelligence software, the MTMM system will also perform the following functions: Alarms, immediate corrective actions, reports, and logs including accounting, recalls to care providers, optimized plans for preventive check-ups and care, optimized management of all personnel, material, devices and infrastructure resources of the caregivers, and provide all sorts of statistics for any level of the medical hierarchy in political, public, and private health organizations and insurers.

FIG. 4 shows a typical 'Piconet' 43 in the MTMM system, having a mobile telephone 41 with display 42, special display control buttons 44, numeric keypad 45 for typing in values from stand-alone tests, and speaker and microphone for voice output and input 46. The mobile telephone 41 communicates with any server on the Internet and its built-in RF-Piconet transceiver 47 communicates with two sensors on the patient's body and one tabletop device.

A heart monitor 50 senses the ECG with two electrodes 48, pre-analyzes the ECG and stores it on a memory-card 49. The heart monitor also monitors the breathing rate and volume by breath sensors 52. The measured values are stored and checked for coherence between two normally independent signals. The heart monitor 50 uses the display 42 of the mobile telephone 41 to show the patient locally his condition, such as with heart-rate, body temperature, breathing rate arid breath volume. The mobile telephone 41 further transmits the condition data over the Internet 53 to the MTMM system and to its Log Manager Module. The heart monitor 50 and mobile telephone 41 may communicate continuously or periodically with each other, only in case of alarms, or in cases when limits are exceeded.

The system has a non-invasive blood pressure unit, 55 which is used only a few times a day according to the doctor's request. Like many other devices; whenever the unit is taken out of the pocket and switched on, it automatically searches via transceiver 47 the area for an active 'Piconet' to connect to. The RF-Piconet transceiver 47 (like Bluetooth) offers this type of network, similar to the wire-bound Ethernet.

An old fashioned strip-type glucose meter 56 may be used with the system. The built-in RF-Piconet transceiver 47 will automatically call the MTMM system via the mobile telephone's access to the Internet 51 and will request the condition measurement schedules. If it does not have the network capability, the MTMM system will request the patient, via the mobile telephone's display 42, to perform a measurement at the prescribed time and to type in the resulting value via the numeric keypad 45 of the mobile telephone 41. It should be clear to the skilled person that instead of mobile telephones, 41 normal telephone sets or PC's with a monitor can also be used.

Built-in data conversion modules in the Log Manager Module allow defined alarms and condition data formats to be transferred directly into the system database. The supervisors can assess the individual patients' status in 'real-time' by calling their mobile phone's "Piconet" hub.

Also, the devices leased and maintained by the caregiver, ambulance personnel, and medical personnel can be called and directed in 'real-time'. The logs of their deployment are transferred, at the same time, to commercial bookkeeping and invoicing systems within the company, offering useful and efficient support that are not found in other systems.
Standard Hardware and Software The system is standard-based, and runs on Windows and Unix platforms. The databases are all relational. The system is also modular. The individual modules can be used independently of one another.

The preferred network, fully exploiting the new WAP (Wireless Application Protocol) capabilities, is the worldwide Internet, or an Intranet in large companies, hospitals, nursing home facilities, etc. The mobile telephone can control several sensors and input devices. In addition, the Bluetooth network is the future standard in these"Piconets".

What is claimed is:

1. A system for maintenance and management of health for large numbers of individual patients, the system comprising:

(a) a condition monitoring device, having alarm signals, that measures physiological data on a patient, and transmits, enters, and stores the data as event information of the patient into a Condition Log;

(b) a supervision device that assesses the alarm signals and event information, wherein the supervision device transmits the alarm signals and event information to caregivers, allowing the caregivers to initiate a corrective action on the patient and to request a report about the corrective action and its results, the report being entered and stored into a Shift Log;

(c) an evaluating device, that evaluates problems and patterns of measurements by comparing the problems and patterns with accumulated information in a knowledge database, wherein the evaluating device thereafter selects the appropriate corrective action to be recommended to the caregivers, requests a report of the caregivers about the corrective action and its results, and enters the report into the knowledge database, whereby the knowledge database accumulates and enlarges, and;

(d) a communication system that connects to a system for transmitting alarms and recommendations to a supervisor, whereby the supervisor corrects and releases the alarms and recommendations, and the alarms and recommendations are transmitted further to the caregivers for performing a recommended action.

2. A system according to claim 1, wherein the communication system further comprises at least one device for Internet access.

3. A system according to claim 1, wherein the communication system further comprises at least one sensor for measuring the physiological data on the patient.

4. A system according to claim 1, wherein the system further comprises a Medical Web Site, the Medical Web Site containing a separate database containing all medical data and a medical history of each individual patient, the database being accessible by the patient and the caregivers.

5. A system according to claim 1, wherein the system further comprises a Personal Health Plan Manager Module, the Personal Health Plan Manager Module being attached to monitored data, compliance for therapies, and outcome of the therapies, and wherein the Personal Health Plan Manager Module is accessible by the patient and the caregivers.

6. A system according to claim 1, wherein the system further comprises a Log Manager Module, and wherein the Log Manager Module monitors the alarm signals and the event information in the Condition Log and supervises the reports in the Shift Log.

7. A system according to claim 1, wherein the system further comprises a Diagnostic Manager Module, wherein the Diagnostic Manager Module diagnoses the condition of the individual patient by comparing data stored in expert computer programs containing diagnosis guidelines to the accumulated data of the knowledge database.

8. A system according to claim 2, wherein the communication system contains at least one device selected from the group consisting of: Internet accessible mobile telephones, personal digital assistants, and personal computers.

9. A system according to claim 5, wherein the Personal Health Plan Manager Module contains a type of data selected from the group consisting of: doctor's prescriptions for medication; treatments, practices, and lifestyles of the individual patient; a schedule for the monitoring of conditions stored in the Condition Log; selection of sensors to be used; threshold values of the physiological data to be monitored; and corrective actions.

* * * * *